(12) United States Patent
Puong et al.

(10) Patent No.: US 8,165,379 B2
(45) Date of Patent: Apr. 24, 2012

(54) METHOD OF PROCESSING RADIOLOGICAL IMAGES, AND, IN PARTICULAR, MAMMOGRAPHIC IMAGES

(75) Inventors: Sylvie Puong, Paris (FR); Serge Louis Wilfrid Muller, Guyancourt (FR); Razvan Iordache, Paris (FR); Xavier Bouchevreau, Issy les Moulineaux (FR)

(73) Assignee: General Electric Company, Schenectady, NY (US)

( * ) Notice: Subject to any disclaimer, the term of this patent is extended or adjusted under 35 U.S.C. 154(b) by 411 days.

(21) Appl. No.: 12/478,943

(22) Filed: Jun. 5, 2009

(65) Prior Publication Data

US 2009/0304253 A1    Dec. 10, 2009

(30) Foreign Application Priority Data

Jun. 6, 2008    (FR) ...................... 08 53763

(51) Int. Cl.
    *G06K 9/00* (2006.01)
    *A61B 6/04* (2006.01)
(52) U.S. Cl. ............................ 382/131; 378/37; 600/431
(58) Field of Classification Search .......... 382/128–144, 382/154, 173, 180, 270; 378/4, 5, 9, 37, 378/98.11; 600/431
See application file for complete search history.

(56) References Cited

U.S. PATENT DOCUMENTS

| 4,837,686 | A | | 6/1989 | Sones et al. |
| 5,046,118 | A | * | 9/1991 | Ajewole et al. ............... 382/169 |
| 6,125,166 | A | | 9/2000 | Takeo |
| 6,173,034 | B1 | | 1/2001 | Chao |
| 6,577,762 | B1 | * | 6/2003 | Seeger et al. ................ 382/173 |
| 6,683,934 | B1 | * | 1/2004 | Zhao et al. ........................ 378/9 |
| 2008/0167552 | A1 | | 7/2008 | Bouchevreau et al. |
| 2011/0157154 | A1 | * | 6/2011 | Bernard et al. ............... 345/419 |

FOREIGN PATENT DOCUMENTS

EP    1113392    7/2001

OTHER PUBLICATIONS

Kappadath S C et al: "Dual-energy digital mammography for calcification imaging: improvement by post-image processing" Proceedings of the SPIE—The International Society for Optical Engineering USA, vol. 5745, No. 1, Apr. 20, 2005, pp. 1342-1350, XP00252149 ISSN: 0277-786X.

Kappadath S et al: "Dual-energy digital mammography for calcification imaging: Scatter and nonuniformity corrections" Medical Physics, AIP, Melville, NY, US, vol. 32, No. 11, Oct. 21, 2005, pp. 3395-3408, XP012075202.

(Continued)

*Primary Examiner* — Hoa Pham
(74) *Attorney, Agent, or Firm* — Global Patent Operation; Jonathan E. Thomas (57) ABSTRACT

A method of processing a radiological image of an organ. The method may comprise generating a recombined image (R) from at least one previously acquired low energy image (L) and one high energy image (H) of a portion of the organ. The recombined image comprises a background and one or more areas corresponding to the presence of a contrast medium in the organ. The method may further comprise correcting the recombined image (R) by compensating (C) for the nonuniformities present in the background to obtain a compensated recombined image in which the background has a substantially uniform grey level.

11 Claims, 4 Drawing Sheets

OTHER PUBLICATIONS

Kappadath S Cheenu et al: "Dual-energy digital mammography for calcification imaging: noise reduction techniques." Physics in Medicine and Biology Oct. 7, 2008, vol. 53, No. 19, Oct. 7, 2008, pp. 5421-5443, XP002512150 issn: 0031-9155.

Wagner, F.C. et al: "Dual-energy x-ray projection imaging: two sampling schemes for the correction of scattered radiation", Medical Physics, 1988, 15 (5), pp. 732-748.

Seibert, J. et al: "X-ray scatter removal by deconvolution", Medical Physics, 1988, 15 (4), pp. 567-575.

Trotter, D.G. et al: "Thickness-dependent scatter correction algorithm for digital mammography", Proceedings of SPIE Medical Image 2002, 4682, pp. 469-478.

* cited by examiner

METHOD OF PROCESSING RADIOLOGICAL IMAGES, AND, IN PARTICULAR, MAMMOGRAPHIC IMAGES

CROSS-REFERENCE TO RELATED APPLICATIONS

This application claims priority under 35 U.S.C. §119(a)-(d) or (f) to prior-filed, co-pending French patent application serial number 0853763, filed on 6 Jun. 2008, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

FIELD OF THE INVENTION

The field of the invention relates to a method of processing radiological images, and, in particular, mammographic images.

DESCRIPTION OF RELATED ART

In the field of radiology, and more particularly in mammography, image acquisition techniques referred to as "dual energy" are known. These techniques consist in injecting a contrast medium (e.g., containing iodine) into tissues in a region of the body being imaged (e.g., a breast), and in then successively acquiring two images referred to as a "low energy image" and a "high energy image." The high and low energy images are acquired by exposing the region of the body to radiation (X-rays) having different spectra or ranges.

Figure 1:
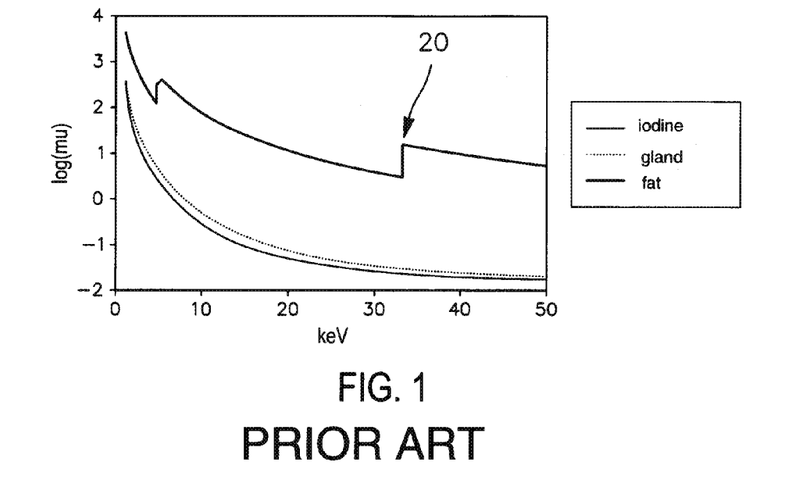
FIG. 1, which has already been discussed, is a graph which schematically represents the absorption coefficient for a contrast medium in relation to the radiation energy.

As shown in FIG. 1, the contrast medium does indeed have a K jump in energy (referenced as 20) corresponding to a sudden increase in the photon attenuation coefficient which occurs when the photon energy is equal to the electron bonding energy of the K layer of the contrast medium atoms interacting with the photons. Commonly used contrast mediums such as iodine and barium, for example, have respective K jumps for X-ray absorption at 33.2 KeV and 37.4 KeV, respectively. The low energy image is acquired by exposing the region being imaged to radiation the energy of which is lower than the K jump of the contrast medium, whereas the high energy image is acquired by exposing the region of the body being imaged to radiation the energy of which is higher than the K jump of the contrast medium.

In the low energy image, attenuation of the radiation via the injected contrast medium is relatively low and the image obtained shows a high degree of contrast between the fatty and glandular tissues. By comparison, the high energy image shows a more significant attenuation of the radiation via the contrast medium, with the result being that the high energy image has a greater degree of contrast between the contrast medium and the surrounding tissues.

In order to enable improved visualization of the areas of the organ containing the contrast medium, the low and high energy images are recombined in order to produce a recombined functional image highlighting the tissue areas marked by the contrast medium.

The recombining operation is aimed at obtaining a recombined functional image wherein, on the one hand, one or more areas appear in which the contrast medium is present, in particular lesion areas, and, on the other hand, a background area having a uniform grey level.

In dual-energy contrast-enhanced digital mammography (DE CEDM) or digital angiomammography, the breast of a patient is compressed so as to have as constant a thickness as possible. Then, two images are acquired successively, by subjecting the area of the body to radiation having different energy spectra or ranges. The low energy and high energy images obtained are recombined in order to obtain a recombined functional image of the contrast medium.

Similarly, in dual-energy contrast-enhanced digital breast tomosynthesis (DE CEDBT), or digital breast angiotomosynthesis, the breast of a patient is compressed, and high energy and low energy projective image sequences are acquired by moving the radiation source about in different positions. This operation can be carried out by successively acquiring a low energy projective image and a high energy projective image at each position of the source, or by first acquiring a sequence of low energy projective images for various positions of the source, and then, secondly, a sequence of high energy projective images for various positions of the source. For each angular position of the source, the corresponding low energy and high energy images are recombined so as to obtain a sequence of recombined images.

The recombination operation can consist of a subtraction operation having the following form:

$$x_s = \log(x_h) - R \cdot \log(x_l)$$

where $x_s$ is the grey level of a pixel of the recombined image, $x_h$ is the grey level of a pixel of the high energy image, $x_l$ is the grey level of a pixel of the low energy image.

In the hypothetical case where the energy spectra of the high and low energy radiation used to acquire the images are monoenergetic, adjustment of the parameter R theoretically makes it possible to delete (or subtract) the organ tissue-related data and to retain only the contrast medium-related data.

However, in actual practice, this recombination technique is not suitable when the radiation energy spectra used are not monoenergetic. In particular, logarithmic subtraction results in the obtainment of a recombined image having nonuniformities in the background area, which are due to the distribution of glandular and fatty tissues within the breast.

In addition, other factors are also the cause of variations in the grey levels appearing in the recombined image.

As a matter of fact, despite being compressed, the breast does not have a uniform thickness. More precisely, the breast includes a compressed portion (interior portion) having a substantially uniform thickness and a non-compressed portion (outer edge portion), in which the thickness of the breast decreases very rapidly.

Variations in breast thickness as well as variations in the scattering component of the tissues in proximity to the outer edge of the breast create variations in grey levels appearing in the background area of the recombined image.

The decrease in breast thickness in proximity to the outer edge of the breast has the effect of increasing the values of the grey levels in the low energy and high energy images when approaching the outer edge of the breast. This increase in the grey levels results in a decrease in the values of the grey levels in the recombined image. Since the recombined image is an image wherein the grey level values are proportional to the thickness of the contrast medium, this decrease is interpreted as a decrease in the presence of the contrast medium in proximity to the outer edge of the breast.

Conversely, the decrease in the scattering component in proximity to the outer edge of the breast has the effect of decreasing the grey levels in the low energy and high energy images when approaching the outer edge of the breast. This reduction in the grey levels in the recombined image is interpreted as an increase in the presence of the contrast medium in proximity to the outer edge of the breast.

Other factors, such as an anode heel effect of the source for the acquisition device, which creates variations in the spectral distribution within the radiation beam produced by the source, can also cause variations in the grey levels within the background area of the recombined image.

These variations in grey level are troublesome for the radiologist, because they make it difficult to view the outer edge portion of the breast without changing the windowing level used to view the interior of the breast (i.e., the compressed area of the breast)

Furthermore, these variations in grey level are likely to be interpreted as signs of the presence of a contrast medium and to result in image interpreting errors.

BRIEF SUMMARY OF THE INVENTION

An embodiment of the invention may be configured to produce a recombined image of improved quality, i.e., wherein the nonuniformities of the background area of the recombined image have been reduced, or even eliminated.

One embodiment provides a method of processing a radiological image of an organ. The method may comprise-generating a recombined image from at least one previously acquired low energy image and one high energy image of a portion of the organ. The recombined image may comprise a background and one or more areas that correspond to the presence of a contrast medium in the organ. The method may also comprise correcting the recombined image by compensating for the nonuniformities present in the background to obtain a compensated recombined image, the background of which has a substantially uniform grey level.

According to one embodiment of this method, the correction step is carried out after the recombination step, which enables elimination of the nonuniformities due to the scattering variations which appear as a result of the recombination of the high and low energy images.

It should be noted that this result could not be obtained by individual compensation performed on each of the high and low energy images prior to the recombination step.

The method enables obtainment of a recombined image having a good visual quality, and potentially enables better detection of possible lesions and improved quantification of the distribution of the contrast medium.

The step for correcting the recombined image preferably includes the application of a compensation image to the recombined image in order to compensate for the nonuniformities present in the background area. This application consists in pixel-by-pixel addition or multiplication of the recombined image to the compensation image.

However, the step for correcting the recombined image may include the application of other compensation treatments, e.g., such as the application of a linear or nonlinear filter enabling elimination of the nonuniformities present in the background area.

In one embodiment of the invention, the method may also comprise: generating a filtered recombined image via extraction of low-frequency spatial components from the recombined image; and generating the compensation image from the filtered recombined image.

Filtering of the low frequencies stems from the observation that the nonuniformities due to scattering variations in the recombined image correspond to low-frequency components, whereas the lesions, in which the contrast medium has accumulated, correspond to higher frequency components.

More precisely, the step for generating a compensation image may comprise one or more sub-steps of: determining a background grey level from a histogram of the recombined image; and calculating the compensation image as the difference between a uniform image having he predetermined grey level and the filtered compensated image.

The compensation image is thus calculated as the complementary image of the recombined image, in order to obtain a uniform grey level throughout the breast.

The sub-step for determining a background grey level includes the determination, from a histogram of the recombined image, of the pixel peak having said grey level.

Furthermore, in one embodiment of the invention, the step for generating a recombined image includes a recombination operation of polynomial form:

$$y = \sum_{i,j} a_{i,j} \cdot \varphi(x_l)^i \cdot \varphi(x_h)^j$$

where y is the grey level of a pixel of the recombined image (R), $x_l$ is the grey level of a pixel of the low energy image (L),
$x_h$ is the grey level of a pixel of the high energy image (H),
$\varphi$ is a function associating a radiological thickness with acquired grey level values,
i and j are integers, and
$a_{i,j}$ predetermined recombination parameters.

The recombination parameters $a_{i,j}$ can be predetermined parameters, which depend on high energy and low energy image acquisition conditions.

In particular, the recombination parameters depend on a compression thickness of the imaged organ and on high and low energy radiation energy spectra to which the organ was subjected during the acquisition operation.

Furthermore, the recombination parameters are predetermined from reference points, the reference points being obtained experimentally via calibration of an acquisition device using a phantom which simulates several tissue compositions and several contrast medium thicknesses, and via calculation using a mathematical model, by varying a tissue composition and contrast medium thickness, and by maintaining constant acquisition conditions.

The step for generating a recombined image preferably includes a recombination operation of the second-degree polynomial type:

$y = a_{0,0} + a_{1,0} \cdot \varphi(x_l) + a_{0,1} \cdot \varphi(x_h) + a_{1,1} \cdot \varphi(x_l) \cdot \varphi(x_h) + a_{2,0} \cdot \varphi((x_l)^2 + a_{0,2} \cdot \varphi(x_h)^2$ where the function $\varphi$ is a logarithmic function.

BRIEF DESCRIPTION OF THE DRAWINGS

Other characteristics and advantages will become more apparent from the following description, which is entirely non-limiting and illustrative, and which should be read with reference to the appended figures, in which.

DETAILED DESCRIPTION OF THE INVENTION

Figure 2:
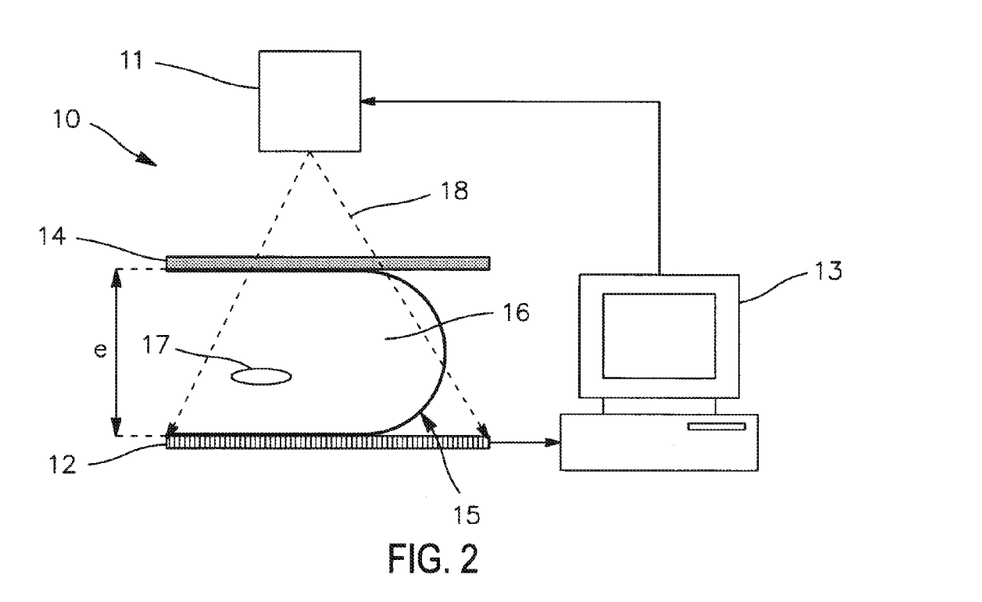
FIG. 2 is a schematic representation of a mammographic image acquisition and processing device in accordance with one embodiment of the invention.

FIG. 2 is a schematic representation of a mammographic image acquisition and processing device 10.

The device 10 includes a source 11 capable of emitting X-rays 18, a digital detector 12 capable of receiving and detecting the rays emitted by the source 11, and a processing unit 13 capable of controlling the source 11 and of receiving and processing images acquired by the detector 12.

One breast 15 of a patient is arranged between the source 11 and the detector 12.

The device 10 also includes a compression plate 14 for compressing the breast 15 so that the breast has a compressed portion of substantially constant thickness.

Prior to this, the breast 15 received an injection of a contrast medium. The breast 15 includes an area of tissue 16 devoid of any contrast medium and one or more areas 17 of tissue in which the contrast medium has accumulated.

The processing unit 13 is capable of controlling the source 11 in order to vary the energy spectrum of the radiation 18 emitted by the source 11. In particular, the processing unit 13 is capable of controlling the source 11 so that it emits a low-energy radiation, the mean energy of which is lower than the K jump of the contrast medium, or a high-energy radiation, the mean energy of which is greater than the K jump of the contrast medium.

The detector 12 is capable of receiving the radiation emitted by the source, after it has passed through the breast tissue 15. The detector 12 generates an image in the form of data comprising a set of pixels, and for each pixel there is an associated grey level. The grey level is representative of the attenuation of the X-rays having passed through the breast tissue.

The detector 12 is capable of transmitting the image thus acquired to the processing unit 13.

The processing unit 13 is programmed to receive the low energy and high energy images and to execute an image processing method in order to generate a recombined image from the low energy and high energy images acquired.

The processing unit 13 can also be programmed to control the display of the recombined image produced on a screen, so that a radiologist can view the recombined image.

In FIG. 2, it is noted that the breast 15 includes a compressed portion (interior portion) with a substantially constant thickness and a non-compressed portion (outer edge portion, most distant from the thoracic cage), wherein the thickness of the breast decreases very rapidly.

Figure 6:
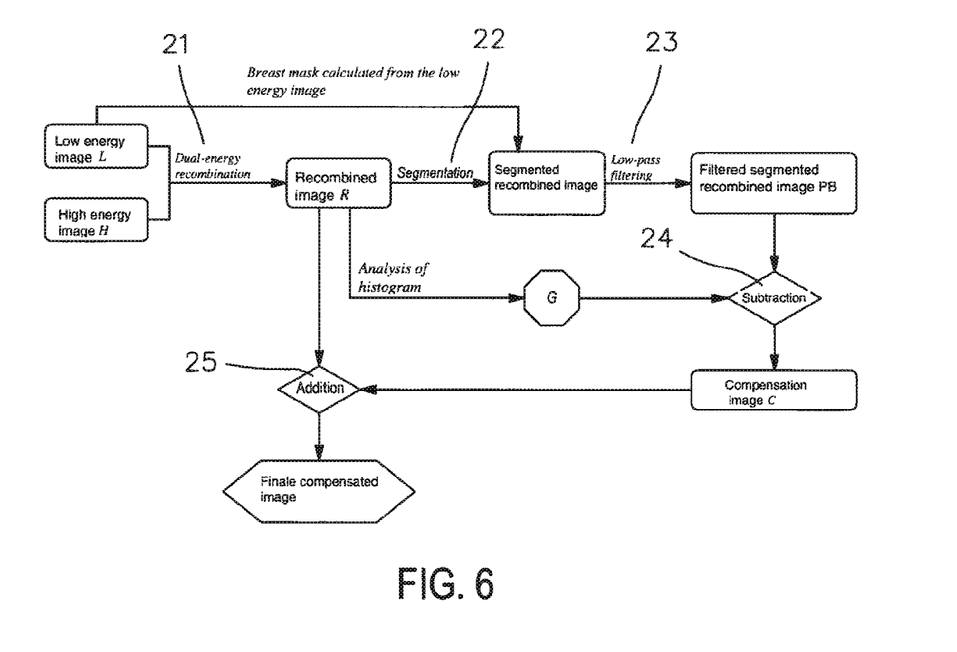
FIG. 6 is a schematic representation of the steps of an image processing method in accordance with one embodiment of the invention.

FIG. 6 is a schematic representation of the steps of an image processing method implemented by the processing unit 13.

A low energy image L and a high energy image H of the patient's breast were acquired previously during an acquisition process.

Furthermore, it is assumed that the compression thickness of the breast and the low energy and high energy radiation spectra emitted by the source during acquisition of the images L and H are known.

The processing unit 13 executes the following steps:

According to a first step 21, the low energy image L and the high energy image H are recombined in order to obtain a recombined composite image R.

The recombined image R is calculated as:

$$y = \sum_{i,j} a_{i,j} \cdot \varphi(x_l)^i \cdot \varphi(x_h)^j$$

where y is the grey level of a pixel of the recombined composite image, R, which is representative of a contrast medium thickness, $x_l$ is the grey level of a pixel of the low energy image L, $x_h$ is the grey level of a pixel of the high energy image H, φ is a function associating a radiological thickness with acquired grey level values, i and j are integers.

The recombination parameters $a_{i,j}$ are predetermined parameters, which are associated with the acquisition conditions, such as the compression thickness of the breast and the energy spectra of high and low energy radiation emitted by the source.

The processing unit selects a series of recombination parameters $a_{i,j}$ on the basis of the compression thickness of the breast, the energy spectra of the high and low energy radiation emitted by the source, as well as a compression thickness correction parameter $\theta_f$.

Parameter $\theta_f$ is obtained via analysis of the low-energy image histogram. A method for obtaining and applying a thickness correction parameter is described, for example, in the document EP 1 113 392 A1.

Figure 7:
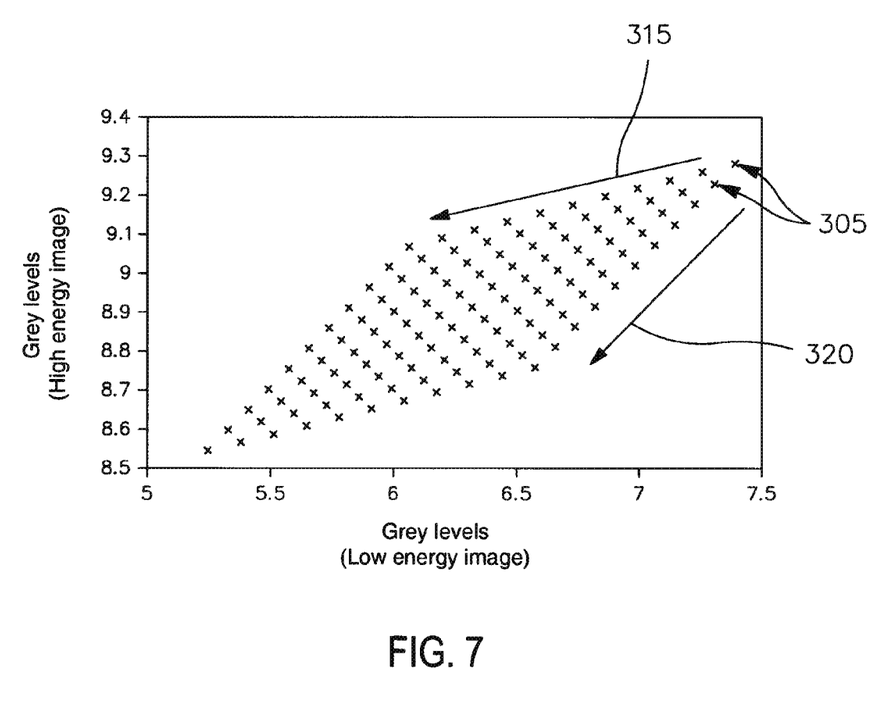
FIG. 7 is a schematic representation of grey level value reference points table drawn at a logarithmic scale, for specific high and low energy image acquisition conditions.

The recombination parameters $a_{i,j}$ were predetermined from a series of reference points $(y, x_l, x_h)$ similar to that of FIG. 7.

The reference points $(y, x_l, x_h)$ can be determined either experimentally, via calibration of the acquisition device using a phantom which simulates several tissue compositions and several contrast medium thicknesses, or via calculation using a mathematical model.

The series of reference points $(y, x_l, x_h)$ is established by varying a tissue composition and contrast medium thickness, and by maintaining constant acquisition and tissue thickness parameters.

In the case where a mathematical model is used, the model simulates the generation of an X-ray energy spectrum, given a potential (kVp) and parameter values representative of the material composition of the radiation source. For example, it is assumed that the data in the table of FIG. 7 is generated in relation to the following energy spectrum values: Mo/Mo 25 kV, 100 mAs for low-energy acquisition and Mo/Cu 49 kV, 160 mAs for high-energy acquisition. The model simulates generation of the X-ray spectrum by receiving as input or by calculating a number of photons generated in the high and low energy spectra. The model likewise simulates the attenuation of the X-ray energy spectra through various tissues of the imaged area having varied thicknesses (e.g., by assuming a thickness of 40 mm), and simulates conversion of the X-ray energy spectrum into the grey level of the pixels detected by the detector. By using this mathematical simulation model, the reference points $(y,x_l,x_h)$ of FIG. 7 can be determined.

The recombination coefficients $a_{i,j}$ are determined by means of linear regression analysis of the series of reference points $(y,x_l,x_h)$.

In one preferred embodiment of the invention, the recombined image R is calculated as a second-degree polynomial equation:

$$y = a_{0,0} + a_{1,0} \cdot \phi(x_l) + a_{0,1} \cdot \phi(x_h) + a_{1,1} \cdot \phi(x_l) \cdot \phi(x_h) + a_{2,0} \cdot \phi(x_l)^2 + a_{0,2} \cdot \phi(x_h)^2$$

The function $\phi$ is typically a logarithmic function. The portion $a_{0,0} + a_{1,0} \cdot \phi(x_l) + a_{0,1} \cdot \phi(x_h)$ of this mathematical equation generally represents a mathematical model for logarithmic subtraction. Other high-order polynomial equations could also be used.

Figure 3:
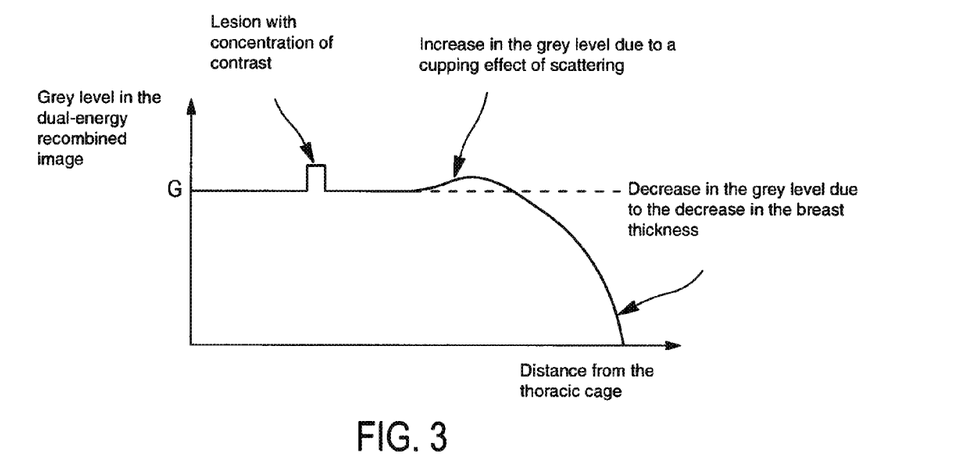
FIG. 3 is a graph which schematically represents a grey level in a recombined image of a compressed breast in relation to the distance from the thoracic cage.

FIG. 3 is a schematic representation of a grey level in the recombined image of the breast in relation to the distance from the thoracic cage.

It is observed that the recombined image has a substantially constant grey level in the compressed portion of the breast closest to the thoracic cage, and a grey level which decreases very rapidly in the outer edge portion of the breast when moving away from the thoracic cage. Furthermore, the compressed portion has localized areas of maximum grey level corresponding to the presence of a contrast medium. In addition, an increase in the grey level is also observed at the transition between the compressed portion and the non-compressed portion of the breast. This artifact is the result of a cupping effect ("cupping artifact") due to modification of radiation scattering in the outer edge portion of the breast.

According to a second step 22, the recombined image R is segmented so as to retain only one area of the image in which the breast appears.

To that end, a masking image is defined from the low energy image, and then the masking image is applied to the recombined image.

The resulting segmented recombined image contains only one area wherein the interior of the breast appears.

Figure 4:
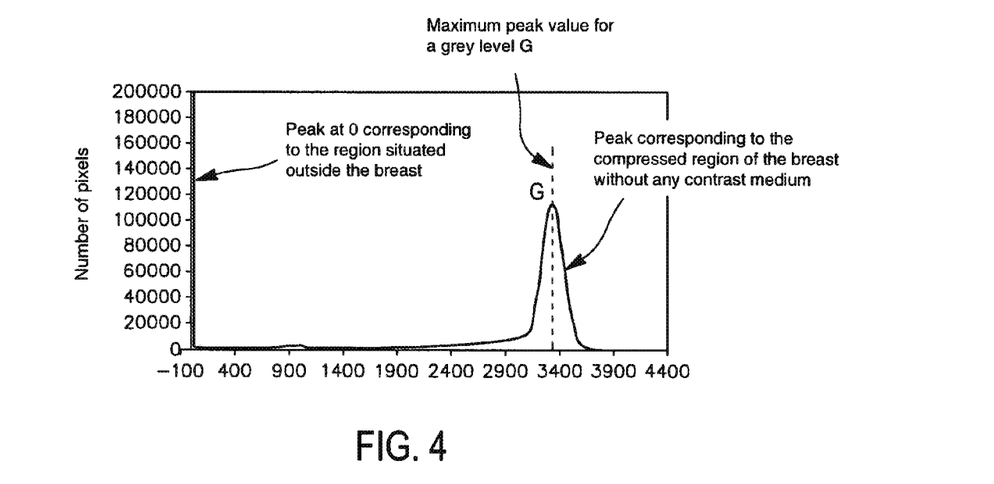
FIG. 4 is a histogram which schematically represents the grey levels observed in a recombined image after segmentation.

FIG. 4 is a histogram of the segmented recombined image representing the number of pixels in the segmented recombined image in relation to the grey level. A first peak is observed for a zero grey level, which corresponds to the image pixels situated outside the breast and a second peak for a grey level G, which corresponds to the grey level of the compressed area of the breast, which does not contain any contrast medium.

According to a third step 23, the segmented recombined image is filtered by means of a low-pass filter capable of selecting the low-frequency spatial components of the image. The low-frequency image obtained PB contains only progressive variations in thickness.

This step is based on the assumption that grey level variations due to scattering variations correspond to low-frequency components of the image, whereas the lesions, in which the contrast medium has accumulated, correspond to higher-frequency components. Consequently, the filtered recombined image PB contains only grey level variations which are due to thickness and scattering variations in the breast.

According to a fourth step 24, a compensation image C is generated.

The compensation image is calculated as the difference between an image having a uniform grey level G and the filtered recombined image PB.

$$C = G - PB$$

where G is the grey level associated with the largest number of recombined image pixels.

The grey level G is determined from the recombined image histogram shown in FIG. 4.

The compensation image C is thus calculated as the complementary image of the filtered recombined image PB, in order to obtain a grey level throughout the entire breast which is equal to G.

According to a fifth step 25, the compensation image C is applied to the recombined image R. More precisely, the compensation image is added to the recombined image so as to obtain a compensated recombined final image:

Compensated recombined final image = R + C

Figure 5:
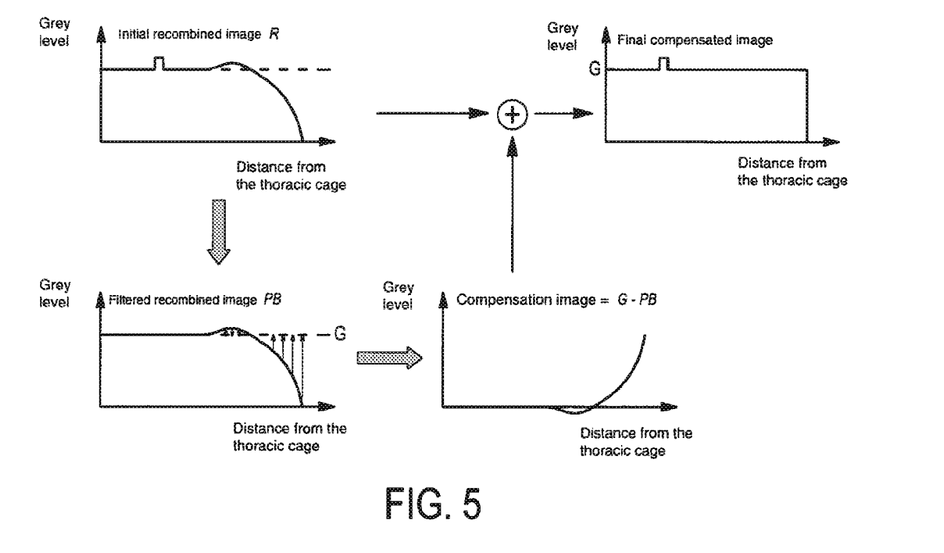
FIG. 5 is a schematic representation of the evolution of the image diagrams over the course of various recombined image processing steps.

FIG. 5 shows the evolution of the image diagrams over the course of various recombined image processing steps.

The compensated recombined final image includes one or more maximum grey level areas corresponding to the presence of a contrast medium and a background area having a uniform grey level G, including the area in proximity to the outer edge of the breast. The scattering effect present in the initial recombined image was eliminated from the final recombined image.

The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the scope of the following claims.

The invention claimed is:

1. A method of processing a radiological image of an organ, the method comprising:
    generating a recombined image (R) from at least one previously acquired low energy image (L) and one high energy image (H) of a portion of the organ, the recombined image comprising a background and one or more areas corresponding to a presence of a contrast medium in the organ; and
    correcting the recombined image (R) by compensating for the nonuniformities present in the background to obtain a compensated recombined final image, the background having a substantially uniform grey level.

2. The method of claim 1, wherein the recombined image correction step comprises:
    applying a compensation image (C) to the recombined image (R) to compensate for the nonuniformities present in the background area.

3. The method of claim 1, further comprising:
    generating a filtered recombined image (PB) via extraction of low-frequency spatial components from the recombined image (R); and
    generating a compensation image (C) from the filtered recombined image (PB).

4. The method of claim 3, wherein the step for generating the compensation image (C) comprises:

determining a background grey level (G) from a histogram of the recombined image (R); and calculating the compensation image (C) as the difference between a uniform image having the predetermined grey level (G) and the filtered recombined image (PB).

5. The method of claim 4, wherein the sub-step for determining a background grey level (G) includes the determination, from a histogram of the recombined image (R), of a pixel peak having said grey level (G).

6. The method of claim 1, wherein the step for generating a recombined image (R) comprises a recombination operation of polynomial form:

$$y = \sum_{i,j} a_{i,j} \cdot \varphi(x_l)^i \cdot \varphi(x_h)^j$$

where y is the grey level of a pixel of the recombined image (R), $x_l$ is the grey level of a pixel of the low energy image (L), $x_h$ is the grey level of a pixel of the high energy image (H), φ is a function associating a radiological thickness with acquired grey level values, i and j are integers, and $a_{i,j}$ recombination parameters.

7. The method of claim 6, wherein the recombination parameters ($a_{i,j}$) are predetermined parameters, which depend on high energy (H) and low energy (L) image acquisition conditions.

8. The method of claim 7, wherein the recombination parameters ($a_{i,j}$) depend on a compression thickness (e) of the imaged organ and on high and low energy radiation energy spectra to which the organ was subjected during the acquisition operation.

9. The method of claim 6, wherein the recombination parameters ($a_{i,j}$) are predetermined from reference points (y,$x_l$,$x_h$), the reference points being obtained experimentally via calibration of an acquisition device using a phantom which simulates several tissue compositions and several contrast medium thicknesses, and via calculation using a mathematical model, by varying a tissue composition and contrast medium thickness, and by maintaining constant acquisition conditions.

10. The method of claim 6, wherein the step for generating a recombined image (R) comprises a recombination operation having the form:

$$y = a_{0,0} + a_{1,0} \cdot \phi(x_l) + a_{0,1} \cdot \phi(X_h) + a_{1,1} \cdot \phi(x_l) \cdot \phi(x_h) + a_{2,0} \cdot \phi(x_l)^2 + a_{0,2} \cdot \phi(x_h)^2.$$

11. The method of claim 6, wherein the function φ is a logarithmic function.

* * * * *